United States Patent
Bocek et al.

(10) Patent No.: US 7,110,814 B2
(45) Date of Patent: *Sep. 19, 2006

(54) HARDWARE/SOFTWARE LOCK FOR SECURE LINKAGE BETWEEN ALGORITHMIC DECISION PROCESS AND CRITICAL SYSTEM FUNCTION EXECUTION

(75) Inventors: Joseph M. Bocek, Seattle, WA (US); Bryan Buchanan, Gig Harbor, WA (US); Tony Harrington, Bellevue, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 434 days.

This patent is subject to a terminal disclaimer.

(21) Appl. No.: 10/647,838

(22) Filed: Aug. 25, 2003

(65) Prior Publication Data

US 2004/0044372 A1    Mar. 4, 2004

Related U.S. Application Data

(63) Continuation of application No. 09/802,321, filed on Mar. 8, 2001, now Pat. No. 6,612,994.

(51) Int. Cl.
 *A61N 1/362* (2006.01)

(52) U.S. Cl. ............................................. 607/9; 607/59

(58) Field of Classification Search .................... 607/5, 607/9, 27, 28, 59
See application file for complete search history.

(56) References Cited

U.S. PATENT DOCUMENTS

| 4,323,966 | A | 4/1982 | Whiteside et al. ........... 364/200 |
| 4,476,869 | A | 10/1984 | Bihn .................... 128/419 PT |
| 5,113,869 | A | 5/1992 | Nappholz et al. ........... 128/696 |
| 5,571,142 | A | 11/1996 | Brown et al. ................... 607/5 |
| 5,660,183 | A | 8/1997 | Chiang et al. .......... 128/695 R |
| 6,021,492 | A | 2/2000 | May ........................... 713/200 |
| 6,266,555 | B1 | 7/2001 | Werner et al. .............. 600/523 |

FOREIGN PATENT DOCUMENTS

EP         1102155       5/2001

*Primary Examiner*—Scott M. Getzow
(74) *Attorney, Agent, or Firm*—Schwegman, Lundberg, Woessner, & Kluth, P.A.

(57) ABSTRACT

An improved protection mechanism to protect from unintended execution of critical tasks operates, in one example embodiment, by receiving a request to start a task by a first process. The first process informs a second process of running an algorithm to verify the legitimacy of the received request to determine the need to start the task. The second process stores the information regarding the starting the algorithm by the first process. The first process runs the algorithm to verify the legitimacy of the received request, and conveys an outcome of the verification to the second process. The second process enables the start of the task by the first process based on the outcome of the verification and a checking of the stored information and the first process starts the task.

26 Claims, 4 Drawing Sheets

HARDWARE/SOFTWARE LOCK FOR SECURE LINKAGE BETWEEN ALGORITHMIC DECISION PROCESS AND CRITICAL SYSTEM FUNCTION EXECUTION

CROSS-REFERENCE TO RELATED APPLICATION(S)

This application is a continuation of U.S. patent application Ser. No. 09/802,321, filed on Mar. 8, 2001, now U.S. Pat. No. 6,612,994, the specification of which is incorporated herein by reference.

TECHNICAL FIELD

The present invention relates generally to protection mechanisms for execution of system critical functions, and more particularly protection mechanisms for execution of system critical functions in a cardiac rhythm management system.

TECHNICAL BACKGROUND

Given the broad spectrum of usage of microcomputers in controlling subsystems of mission critical systems, it is of utmost importance that the interface between the microcomputers and system elements implementing critical functions remain safe during fault conditions within the microcomputer. Such fault conditions may occur in either hardware or software part of the microcomputers. One such example is an unintended execution of otherwise normal software code due to incorrect state information such as program counter value, corrupt stack pointer or stack contents.

One class of mission critical systems is implantable cardiac rhythm management systems, in which electrical therapy is delivered to the heart. The same therapy sequences that are life sustaining may be life threatening if delivered with inappropriate timing. The decision to deliver electrical therapy generally involves the execution of complex algorithms that must be correctly executed to insure the appropriateness of delivered therapy. In the event of fault conditions that compromise the ability of the system to correctly execute such an algorithm, it is critical that inappropriate therapy be blocked, and that the system operation be restored as quickly as possible.

Generally hardware and software locks are used to protect such system critical functions from inadvertent actuation. It is generally desired that such protection mechanisms be effective and efficient in requiring minimum hardware and software to provide satisfactory protection. Furthermore, it is desirable that the latency to actuation be well controlled and that the interval of time during which a critical task is accessible be short and well defined. Protection mechanisms that are effective in preventing unintended unlocking of actuation due to random processor actions are straightforward. They are generally a unique, necessary, and sufficient sequence of a software code (interacting with hardware), which is sufficiently unlikely to have been replicated either by localized or by non-localized random processor action.

Generally the method employed by mechanisms protecting against inappropriate therapy activation involves providing some degree of complexity in the interface to the hardware that activates the therapy. This can be illustrated, for example, with an interface to a microcomputer, that requires more than one bit be set in the input/output space before activation of the critical therapy can occur. Requiring a specific order or time sequence for setting the bits further restricts possible inadvertent activation, as does placing the bits at different input/output locations. With an interface of sufficient complexity, it is extremely unlikely that random activations of the interface by a malfunctioning subsystem or subsystems will result in therapy delivery.

This protection mechanism can generally be enhanced by placing a time limit on unlocking an actuation of a particular critical task, such that the likelihood of random actuation of that task in combination with the specific code to unlock that task within the requisite time period is even more unlikely. It is important to note that there is a limit to the efficacy of a software code sequence in preventing unintended random unlocking of actuation. To illustrate, assume that the unlocking software sequence is sufficiently improbable that only one occurrence of it exists in a device memory, and that occurrence is an intended key that unlocks the critical task. Further assume that this code fragment is protected from being "run over" by a runaway processor and/or by software reset opcodes that precede it in memory. Under these assumptions, the only single random event that can cause execution of the fragment is if the instruction pointer is somehow pointed exactly at unlocking. This is not altogether an improbable event though the probability of its occurring is generally on the order of $2^{-16}$ or greater. Generally, however, such hardware locks are fairly easy to circumvent and by themselves afford little to no protection against unintended execution. Therefore, there is a need for an improved mechanism to protect from an unintended execution of critical tasks.

SUMMARY OF THE INVENTION

According to one aspect of the present subject matter, a request to start a task is received by a first process. Then the first process informs a second process of running an algorithm to verify the legitimacy of the received request, determining the actual need to start the task. Then the second process stores the information regarding the starting of the algorithm by the first process. Then the first process runs the algorithm to verify the legitimacy of the received request, and conveys an outcome of the verification to the second process. Then the second process enables the start of the task by the first process based on the outcome of the verification and a checking of the stored information. Then the first process starts the task. In one embodiment the first process sets an interprocess token upon receiving the request to start the task. In another embodiment the first process unlocks a hardware/software lock upon enabling by the second process to start the task.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

BRIEF DESCRIPTION OF THE DRAWINGS

In the drawings, like numerals describe substantially similar components throughout the several views. Like numerals having different letter suffixes represent different instances of substantially similar components.

DETAILED DESCRIPTION

Figure 1:
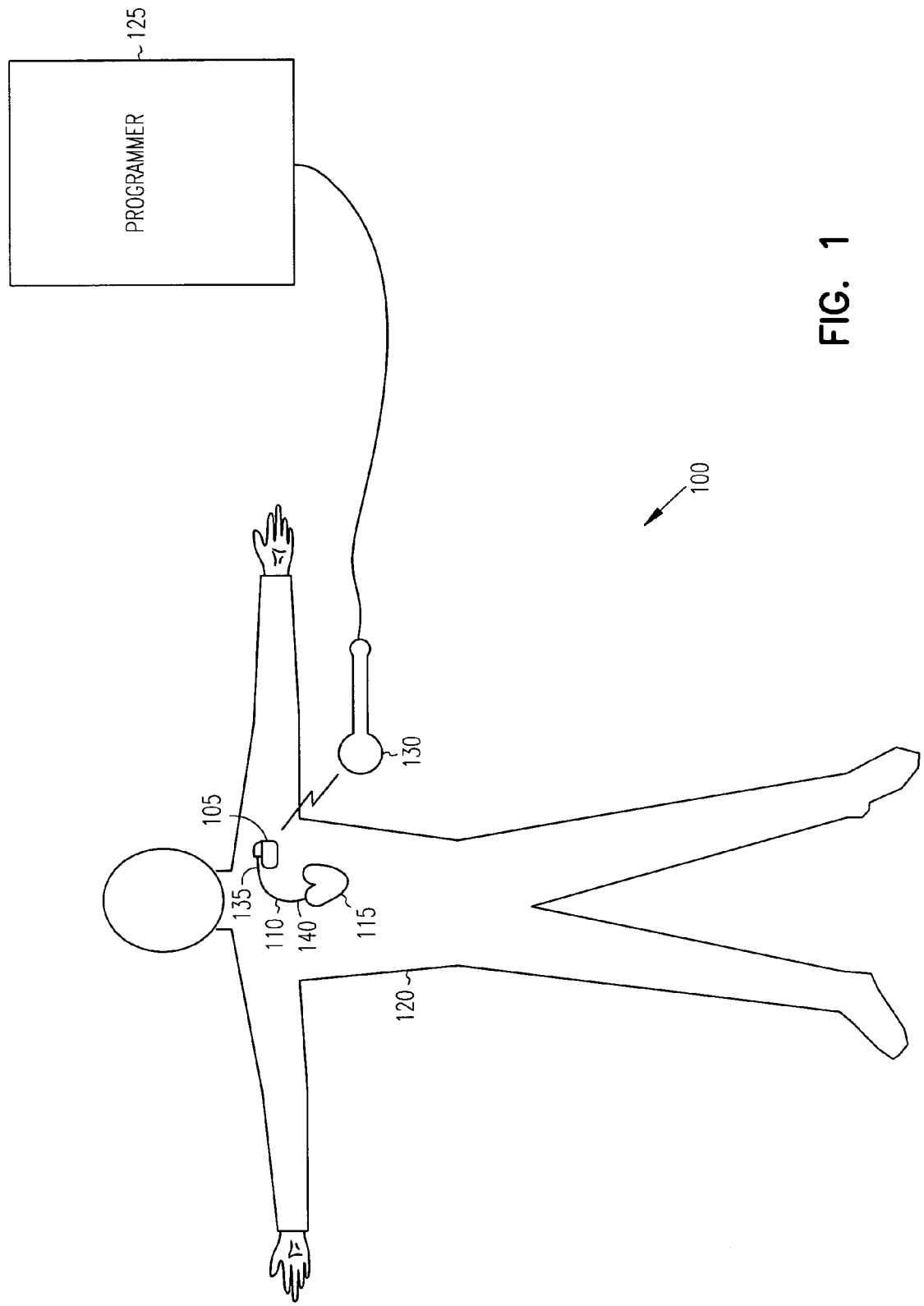
FIG. 1 is schematic/block diagram illustrating generally one embodiment of portions of a cardiac rhythm management including a system to prevent inadvertent actuation of a task and an environment in which it is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents. In the drawings, like numerals describe substantially similar components throughout the several views. Like numerals having different letter suffixes represent different instances of substantially similar components.

In this document the term hardware token is understood as requiring a specific order or time sequence for setting bits in a memory location that further restricts possible inadvertent activation. The term interprocess token refers to one process informing another process of running an algorithm to verify a legitimacy of a request to start a task by setting a token. The term hardware/software lock refers to an interface between a microcomputer and system elements implementing critical decisions having an ability to correctly execute system critical functions. Also, the term task refers to tasks such as delivering a high-energy electrical therapy to a heart experiencing cardiac arrhythmias such as atrial flutter, atrial and/or ventricular cardioversion/defibrillation and/or pacing therapy to a heart. The terms task and critical task are used interchangeably throughout the document.

General System Overview

This document describes, among other things, an improved mechanism to protect from unintended execution of critical tasks. Other aspects of the invention will be apparent on reading the following detailed description of the invention and viewing the drawings that form a part thereof.

Referring now to FIG. 1, there is shown one example embodiment of a schematic/block diagram illustrating portions of a cardiac rhythm management system 100 and an environment in which the present invention can be used. In FIG. 1, system 100 includes an implantable cardiac rhythm management device 105, also referred to as an electronics unit, which is coupled by an intravascular endocardial lead 110, or other lead, to a heart 115 of a patient 120. System 100 also includes an external programmer 125 providing wireless communication with device 105 using a telemetry device 130, and a distal end 140, which is coupled to one or more portions of the heart 115.

Figure 2:
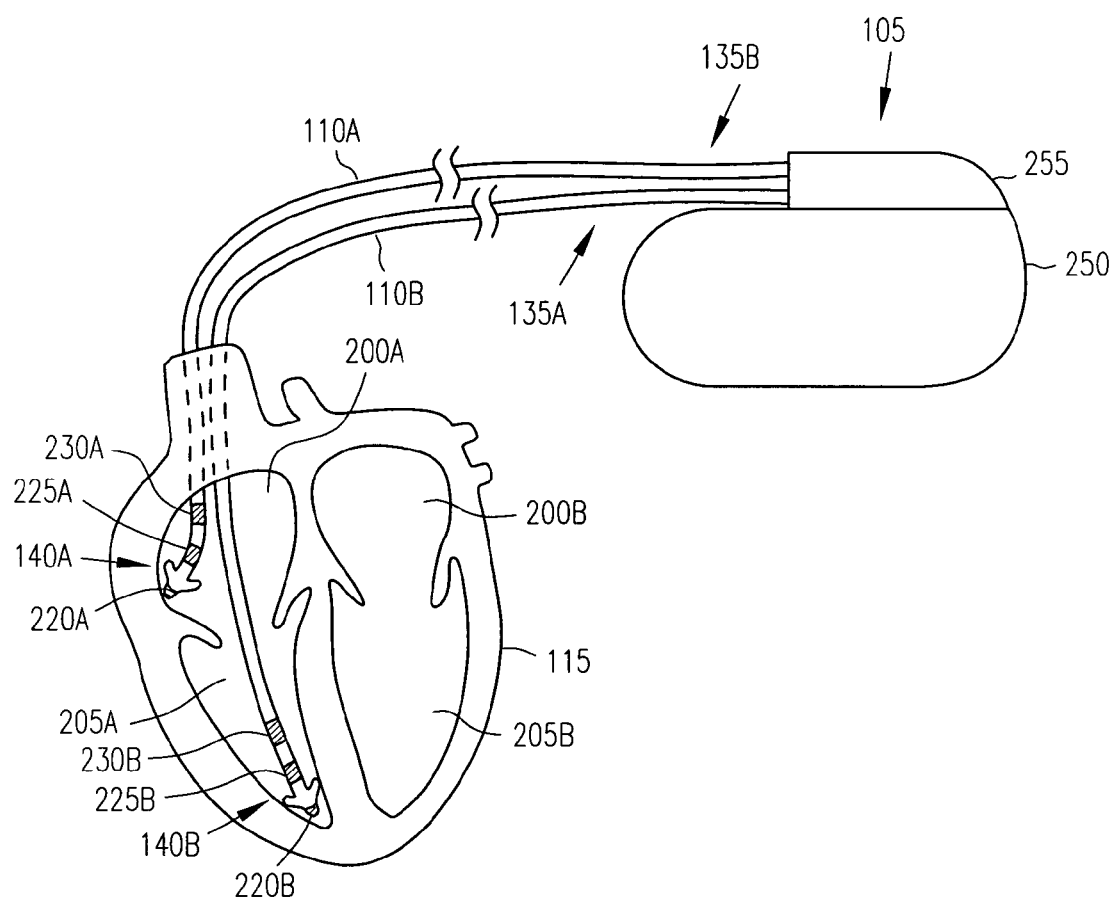
FIG. 2 is a schematic drawing illustrating generally one embodiment of portions of a cardiac rhythm management device coupled to the heart shown in FIG. 1 by a right a trial electrode and a right ventricular electrode.

Referring now to FIG. 2, there is shown a schematic drawing illustrating generally one embodiment of portions of the cardiac rhythm management device 105 electrically-coupled with the heart 115 by right atrial lead 110A and right ventricular lead 110B. The heart shown in FIG. 2, includes a right atrium 200A, a left atrium 200B, a right ventricle 205A, and a left ventricle 205B. In this embodiment, the lead 110A includes electrodes (electrical contacts) disposed in, around, or near a right atrium 200A of the heart 115, such as a ring electrode 225A and tip electrode 220A, for sensing signals and/or delivering therapy to the heart's right atrium 200A. Also in this embodiment, the lead 110B includes electrodes disposed in, around, or near a right ventricle 205A of the heart 115, such as a ring electrode 225B and tip electrode 220B, for sensing signals and/or delivering therapy to the heart's right ventricle 205A. Leads 110A and B optionally also include additional electrodes, such as for delivering atrial and/or ventricular cardioversion/defibrillation and/or pacing therapy to the heart 115. Device 105 includes components that are enclosed in a hermetically sealed can 250. Additional electrodes may be located on the can 250, or on an insulating header 255, or on other portions of device 105, for providing unipolar pacing and/or defibrillation energy in conjunction with the electrodes disposed in or around the heart 115.

Figure 3:
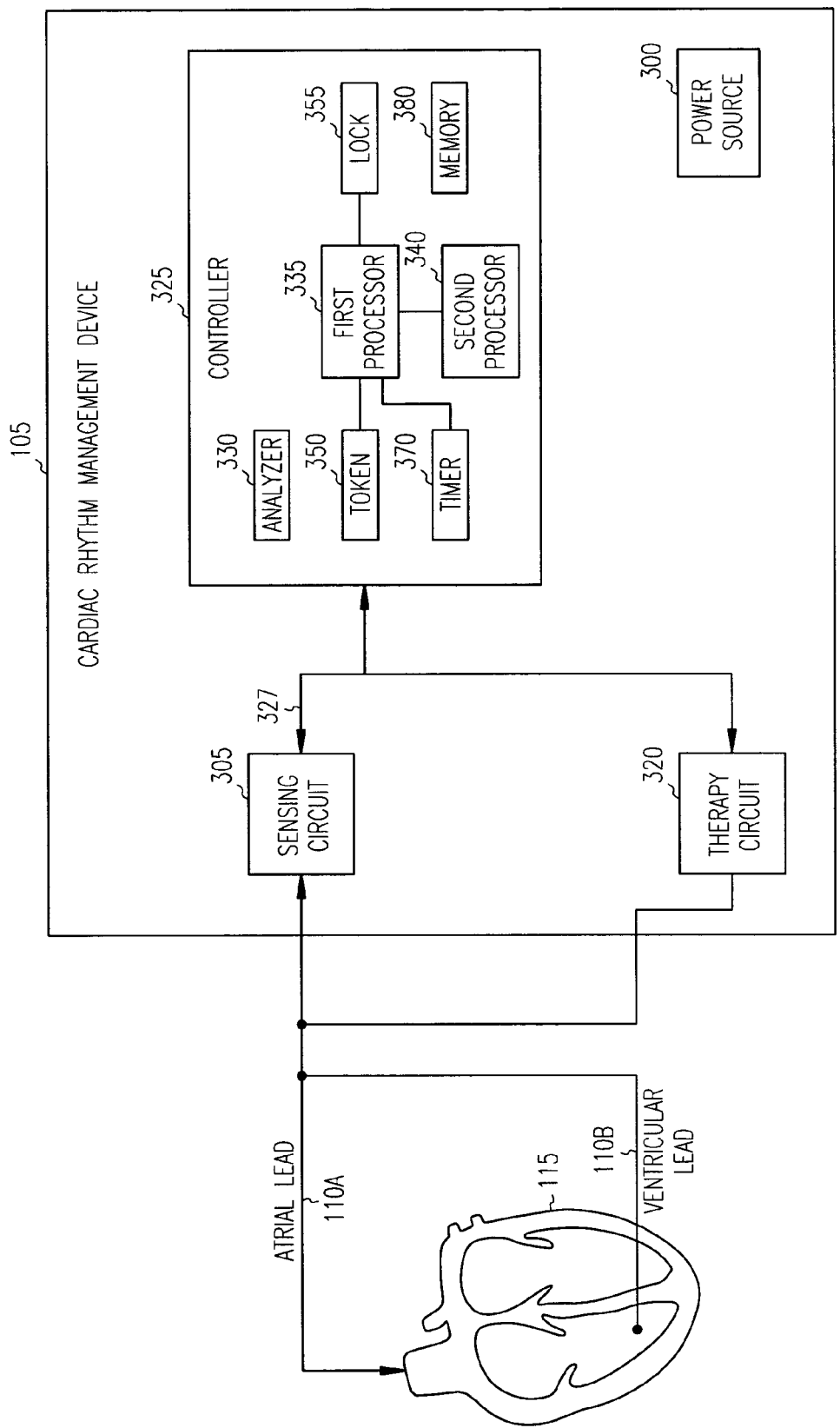
FIG. 3 is a schematic/block diagram illustrating generally one embodiment of portions of a cardiac rhythm management system including a system to prevent inadvertent actuation of a task according to the teachings of the present invention.

Referring now to FIG. 3, there is shown by way of example, but not by way of limitation, one embodiment of portions of the cardiac rhythm management device 105, which is coupled with the heart 115. Device 105 includes a power source 300, and a controller 325. The device 105 includes a sensing circuit 305, an analyzer 330, a therapy circuit 320.

Sensing circuit 305 is coupled by atrial lead 110A and ventricular lead 110B to the heart 115 for receiving, sensing, and/or detecting electrical heart signals. Such heart signals can include atrial activations (also referred to as depolarizations or P-waves) which correspond to ventricular contractions. Such heart signals can include coordinated and uncoordinated cardiac rhythms. Such signals provided to the analyzer 330 can indicate, among other things, the presence of a cardiac arrhythmia. In one embodiment, the signals indicate atrial fibrillation and atrial flutter. Controller 325 also controls the delivery of therapy provided by the therapy circuit 320 and/or other circuits, as discussed below.

Controller 325 includes various modules, which are implemented either in hardware or as one or more sequences of steps carried out on a microprocessor or other controller. Such modules are illustrated separately for conceptual clarity; it is understood that the various modules of controller 325 need not be separately embodied, but may be combined and/or otherwise implemented, such as in software/firmware.

In general terms, the sensing circuit 305 senses electrical signal from a heart tissue in contact with a catheter lead 110A or 110B to which the sensing circuit 305 is coupled. A sensed cardiac signal from the sensing circuit 305 is then received and processed by the analyzer 330 for the presence of a cardiac arrhythmia such as atrial fibrillation, atrial flutter, and/or ventricular cardioversion. Then the analyzer issues a request to a first processor 335 to start delivering a high-energy electrical therapy to the heart 115 based on the outcome of the analysis. Upon receiving the request to start a task such as delivering the high-energy electrical therapy by the first processor 335, the first processor 335 sets an interprocess token 350.

The controller 325 further includes a second processor 340 coupled to the first processor 335. The second processor 340 receives a first message from the first processor 335 about running an algorithm to verify a legitimacy of the received request to start delivering the high-energy electrical therapy. Upon receiving the first message from the first processor 335, the second processor 340 stores the received first message. Then the first processor 335 starts running the algorithm to verify the legitimacy of the request to start delivering the high-energy electrical therapy and sends a second message comprising an outcome of the verification to the second processor 340. Then the second processor 340 enables the start of delivering the high-energy electrical therapy by the first processor 335 based on the outcome of the verification. The controller 325 further includes a hardware/software lock 355 coupled to the first processor 335. The first processor 335 unlocks the hardware/software lock 355 to start delivering the high-energy electrical therapy upon enabling by the second processor 340 and further based on the status of the setting of the interprocess token 350.

In some embodiments, the high-energy electrical therapy is pacing pulse electrical energy. The high-energy electrical therapy can be a defibrillation pulse electrical energy. The first and second processors 335 and 340 can be microprocessors or microcomputers. In some embodiments, the device 105 further includes a timer 370 coupled to the first processor 335, to provide a predetermined variable delay in electrical energy delivered through the electrodes 110B. The term critical task can mean a system critical function such as delivering a high-energy electrical therapy to the heart 115. In some embodiments, the first processor 335 starts an error checking routine when the task is not enabled by the second processor 340. In some embodiments, the first processor clears the interprocess token 350 after starting the task such as delivering the high-energy electrical therapy to the heart 115. The controller 325 can further include a memory 380. The setting of the interprocess token 350 can include writing to one or more memory locations in the memory.

Figure 4:
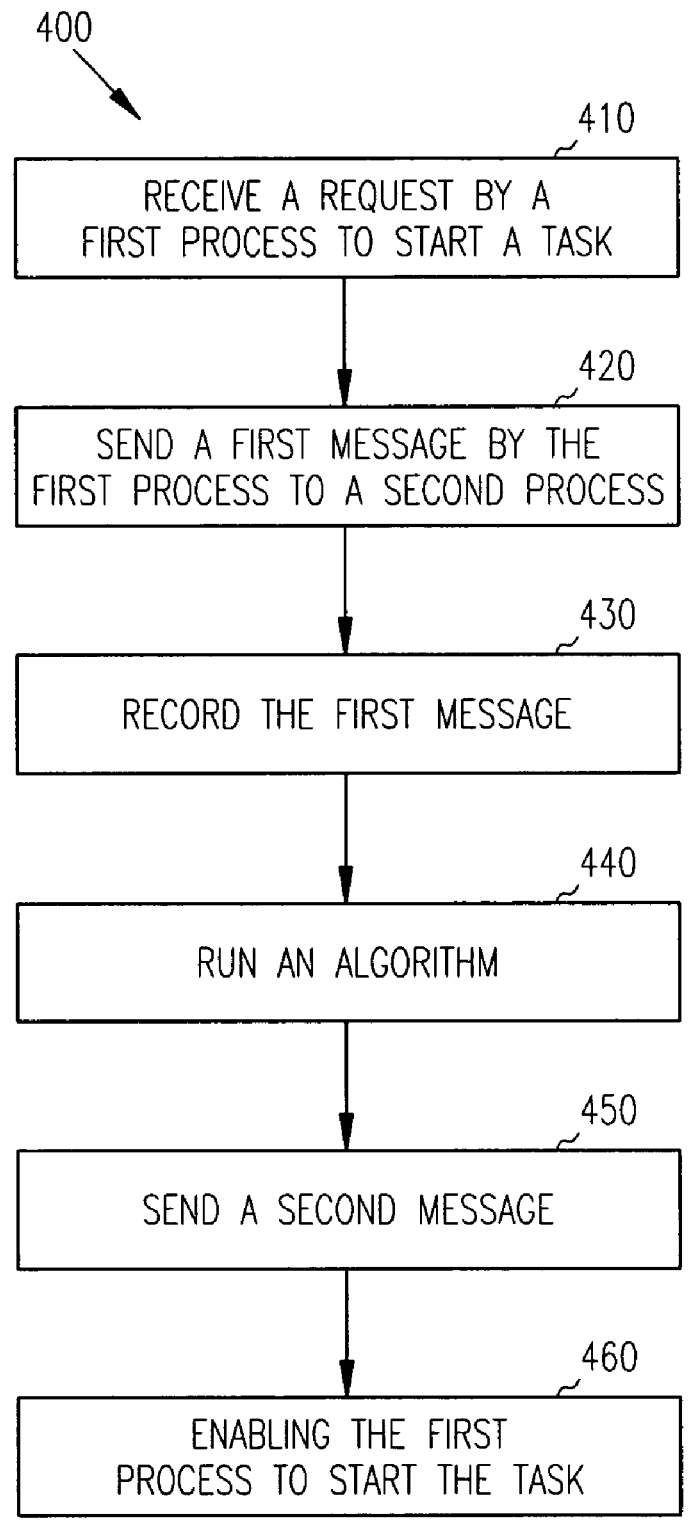
FIG. 4 is a flow diagram illustrating generally one embodiment of operation of the present subject matter.

Referring now to FIG. 4, there is shown one embodiment of a method 400 of preventing an inadvertent actuation of a task in the event of a system failure according to the teachings of the present subject matter. At 410, a first process receives a request to start a task. At 420, the first process sends a first message regarding running an algorithm to verify the legitimacy of the received request to start the task, where the first message is sent to a second process. At 430, the second process records the first message sent by the first process. At 440, the first process runs the algorithm to verify the legitimacy of the request to start the task. At 450, the second process sends a second message indicating the need to start the task to the first process based on the outcome of the verification by the first process. At 460, the second process enables the first process to start the task based on checking the receiving of the first message from the first process.

In some embodiments, the first process sets an interprocess token upon receiving a request to start the task. The setting of the interprocess token can include writing to one or more memory locations. The first message can include informing the second process of setting the interprocess token by the first process. The method 400 can further include recording the setting of the interprocess token by the second process upon receiving information of setting of the interprocess token by the first process. The algorithm can include software code to verify the legitimacy of the request to start the task. The second message can include requesting permission to start the task based on the outcome of the verification. The second message can also include an attempt to start the task based on the outcome of the verification. The method 400 can require the second process to enable the start of the task by the first process upon receiving the second message, and further based on the outcome of the checking of the status of the interprocess token. The method 400, can include setting a hardware/software lock upon enabling by the second process. The setting of the hardware/software lock can include unlocking the hardware/software lock to start the task.

The method 400, can further include running an error checking routine and clearing the interprocess token when the second message by the first process to the second process to start the task is not legitimate. Further, the method 400 can include running the error checking routine and the clearing the interprocess token when the second process does not enable the start of the task by the first process upon checking the status of the interprocess token. Also, the method 400 can include running the error checking routine when the hardware/software lock cannot be unlocked because the interprocess token is not set. The error checking routine under the above mentioned circumstances can be run by the first process. The method 400 can include clearing the interprocess token after starting the task. The task can include a system critical function such as delivering a high-energy electrical therapy to a heart. The system can be a cardiac rhythm management system, such as the one described with reference to FIG. 1.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

CONCLUSION

The above described system provides, among other things, an improved protection mechanism to protect from unintended execution of critical tasks such as inadvertent actuation of critical task due to a system failure.

What is claimed is:

1. An implantable medical device to perform a therapy, the device comprising:
   a therapy circuit for use to provide the therapy;
   a sensing circuit to sense a need and send a request for the therapy; and
   a controller coupled to the sensing circuit and the therapy circuit, the controller to receive a request for the therapy, and upon receiving the request, the controller to perform a process, including:
      setting a token for use to unlock the therapy;
      running an algorithm to insure the legitimacy of providing the therapy, and executing an unlock code to insure an appropriate outcome for the algorithm; and
      unlocking the therapy when the token is set and when the outcome for the algorithm is appropriate.

2. The device of claim 1, wherein the therapy includes electrical therapy to a heart.

3. The device of claim 2, wherein the electrical therapy includes pacing therapy.

4. The device of claim 2, wherein the electrical therapy includes high energy electrical therapy.

5. The device of claim 1, wherein:
running an algorithm to insure the legitimacy of providing the therapy, and executing an unlock code to insure an appropriate outcome for the algorithm:
  writing a first message to a first memory address before running the algorithm;
  running the algorithm to insure the appropriateness of providing the therapy; and
  writing a second message to a second memory address after running the algorithm; and
unlocking the therapy when the token is set and when the outcome for the algorithm is appropriate includes unlocking the critical therapy when the first and second messages indicate the outcome for the algorithm is appropriate.

6. The device of claim 1, wherein setting a token includes writing to one or more memory locations.

7. The device of claim 1, wherein running an algorithm includes running an error checking routine.

8. The device of claim 1, wherein the appropriate outcome for the algorithm includes an indication that the critical therapy is appropriate and an indication that the algorithm was run in its entirety.

9. An implantable medical device in communication with electrical activity of a heart, the device comprising:
at least one electrode adapted to sense electrical signals related to the electrical activity and adapted to deliver electrical therapy to the heart;
a sensing circuit coupled to the at least one electrode to provide electronic signals representative of the electrical activity;
a therapy circuit coupled to the at least one electrode to deliver the electrical therapy; and
a controller coupled to the sensing circuit and therapy circuit, the controller to perform a process, including:
  receiving a request for the therapy based on the electronic signals representative of the electrical activity of the heart;
  setting a token for use to unlock the therapy;
  verifying the legitimacy of the request for the therapy process, including running an algorithm to insure the appropriateness of providing the therapy, and executing an unlock code to insure a satisfactory outcome for the algorithm; and
  unlocking the therapy when the outcome of the algorithm is satisfactory and the token is set to indicate the therapy is appropriate.

10. The device of claim 9, wherein:
running an algorithm to insure the appropriateness of providing the critical therapy, and executing an unlock code to insure a satisfactory outcome for the algorithm includes:
  writing a first message to a first memory address before running the algorithm;
  running the algorithm to insure the appropriateness of providing the critical therapy; and
  writing a second message to a second memory address after running the algorithm; and
unlocking the critical therapy when the token is set and when the outcome for the algorithm is satisfactory includes unlocking the critical therapy when the first and second messages indicate the outcome for the algorithm is satisfactory.

11. The device of claim 10, wherein:
the device further includes memory;
writing a first message includes writing a first value to a first memory location; and
writing a second message includes writing a second value to a second memory location.

12. The device of claim 11, wherein the first and second memory locations include hardware registers.

13. The device of claim 9, wherein setting a token includes writing to one or more memory locations.

14. The device of claim 9, wherein the electrical therapy includes pacing therapy.

15. The device of claim 9, wherein the electrical therapy includes high energy electrical therapy.

16. The device of claim 9, wherein running an algorithm includes running an error checking routine.

17. A method, comprising:
receiving a request for a therapy;
setting a token for use to unlock the therapy;
to verify the legitimacy of the request for the therapy process, running an algorithm to ensure the appropriateness of providing the therapy, and executing an unlock code to insure that running the algorithm results in a satisfactory outcome; and
unlocking the therapy when the token is set and running the algorithm results in a satisfactory outcome.

18. The method of claim 17, wherein unlocking the therapy when the token is set and running the algorithm results in a satisfactory outcome includes unlocking the therapy when the token is set and running the algorithm results in an indication that the therapy is appropriate and an indication that the algorithm was run in entirety.

19. The method of claim 17, wherein running an algorithm includes executing an error-checking routine.

20. The method of claim 17, further comprising rejecting the request for therapy when the token and the first and second messages do not indicate that the therapy is appropriate and that the algorithm was run in its entirety.

21. The method of claim 17, wherein the therapy includes electrical therapy from an implantable medical device.

22. A method, comprising:
receiving a request for a therapy;
setting a token for use to unlock the therapy;
writing a first message prior to running the algorithm;
running the algorithm to ensure the appropriateness of providing the therapy
writing a second message to indicate an outcome resulting from running the algorithm; and
unlocking the therapy when the token and the first and second messages indicate that the therapy is appropriate and that the algorithm was run in its entirety.

23. The method of claim 22, wherein unlocking the therapy when the token and the first and second messages indicate that the therapy is appropriate and that the algorithm was run in its entirety includes unlocking the therapy when the token and the first and second messages result in an indication that the therapy is appropriate and an indication that the algorithm was run in its entirety.

24. The method of claim 22, wherein running an algorithm includes executing an error-checking routine.

25. The method of claim 22, further comprising rejecting the request for therapy when the token and the first and second messages do not indicate that the therapy is appropriate and that the algorithm was run in its entirety.

26. The method of claim 22, wherein the therapy includes electrical therapy from an implantable medical device.

* * * * *